(12) United States Patent
Waid et al.

(10) Patent No.: US 9,581,580 B2
(45) Date of Patent: *Feb. 28, 2017

(54) MEASUREMENT TOOL AND METHOD OF USE

(71) Applicant: Precision Energy Services, Inc., Fort Worth, TX (US)

(72) Inventors: Margaret Cowsar Waid, Aledo, TX (US); Bryan W. Kasperski, Carrollton, TX (US); Michael Andrew Yuratich, Hamble (GB)

(73) Assignee: Precision Energy Services, Inc., Houston, TX (US)

( * ) Notice: Subject to any disclaimer, the term of this patent is extended or adjusted under 35 U.S.C. 154(b) by 782 days.

This patent is subject to a terminal disclaimer.

(21) Appl. No.: 13/661,676

(22) Filed: Oct. 26, 2012

(65) Prior Publication Data

US 2013/0049773 A1 Feb. 28, 2013

Related U.S. Application Data

(63) Continuation of application No. 12/236,591, filed on Sep. 24, 2008, now Pat. No. 8,324,912.

(30) Foreign Application Priority Data

Sep. 27, 2007 (GA) .................. 0718851.9

(51) Int. Cl.
 *G01R 27/26* (2006.01)
 *G01N 33/28* (2006.01)
 *G01N 27/22* (2006.01)
(52) U.S. Cl.
 CPC ....... *G01N 33/2823* (2013.01); *G01N 27/221* (2013.01)

(58) Field of Classification Search
 CPC ............. G01N 33/2823; G01N 27/221; G01N 27/023; G01N 27/025
 (Continued)

(56) References Cited

U.S. PATENT DOCUMENTS 4,751,842 A * 6/1988 Ekrann et al. ............... 73/61.44
4,962,815 A 10/1990 Schultz
(Continued)

FOREIGN PATENT DOCUMENTS

EP 0706045 B1 2/2002
GB 2428483 A 1/2007
(Continued)

OTHER PUBLICATIONS

Ceralloy® Silicon Nitride Ceramics Data Sheet, available as of Aug. 24, 2007 at http://web.archive.org/web/20061017115650/http://www.ceradyne.com/Uploads/Silicon_Nitride_Data_Sheet_08-06.pdf.

(Continued)

*Primary Examiner* — Daniel Miller
(74) *Attorney, Agent, or Firm* — Blank Rome LLP

(57) ABSTRACT

This invention relates to a measurement tool and method of use, and in particular to a measurement tool for use in determining a parameter of a stationary or moving fluid. The measurement tool has been designed primarily for use in borehole formation testing. The measurement tool can measure the dielectric constant of a fluid within a pipe or surrounding the tool. The pipe or wall between the tool and the fluid is electrically insulating. The tool has pair of capacitor plates mounted adjacent to the pipe or wall, a signal generator which can deliver an alternating electrical signal to at least one of the capacitor plates, and a detector for measuring a signal dependent upon the electrical capacitance between the capacitor plates. The measurement tool (Continued)

Figure 1:
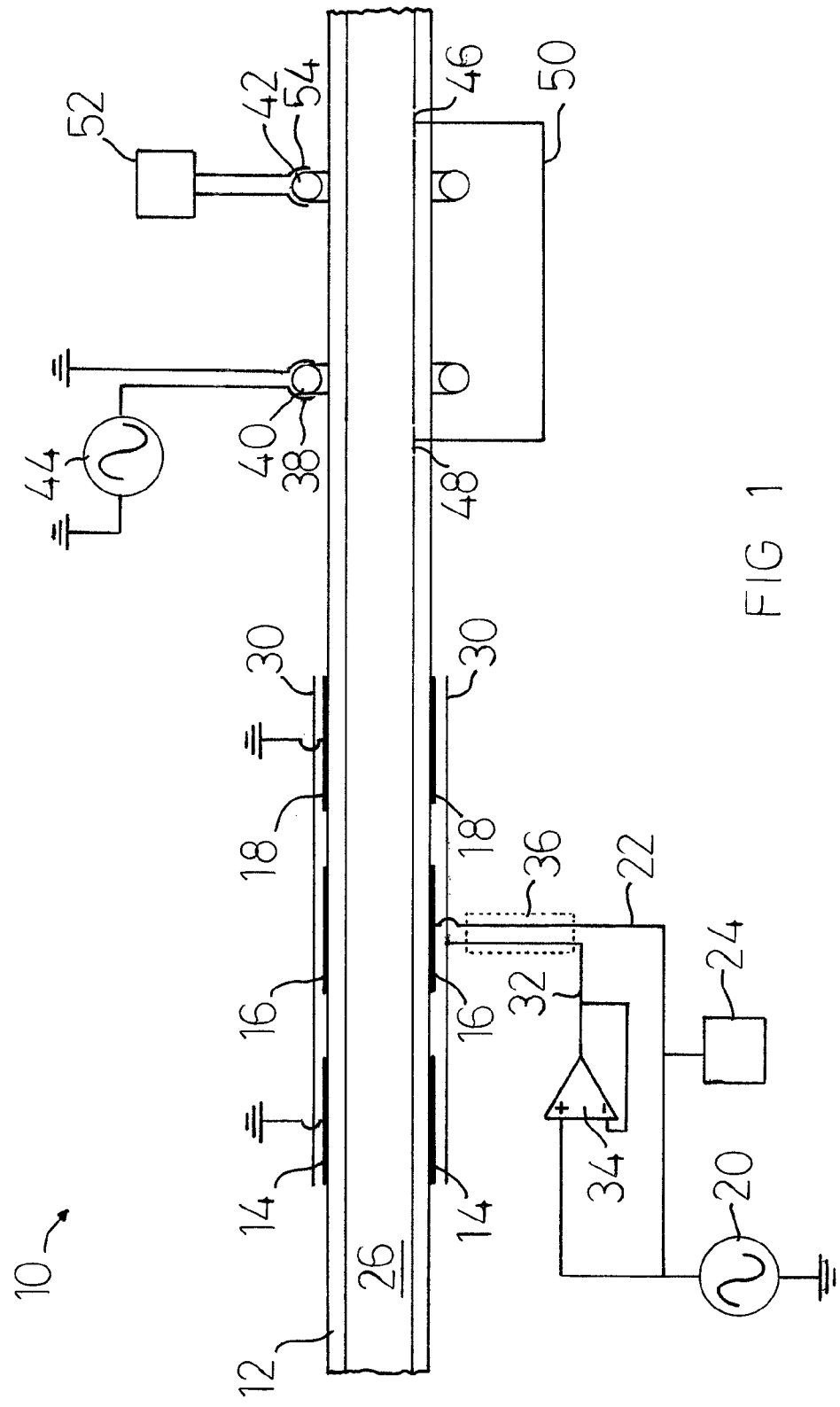

can additionally measure the electrical resistivity of the fluid.

23 Claims, 5 Drawing Sheets

(58) Field of Classification Search
USPC ........ 324/324, 345–347, 354–359, 439–450, 324/658–663, 691, 693, 698
See application file for complete search history.

(56) References Cited

U.S. PATENT DOCUMENTS

| | | | |
|---|---|---|---|
| 5,068,618 | A | 11/1991 | Fry et al. |
| 5,166,679 | A | 11/1992 | Vranish et al. |
| 5,223,796 | A | 6/1993 | Waldman |
| 5,602,334 | A | 2/1997 | Proett et al. |
| 5,934,374 | A | 8/1999 | Hrametz et al. |
| 6,301,959 | B1 | 10/2001 | Hrametz |
| 6,462,562 | B1 | 10/2002 | Svoboda et al. |
| 6,668,924 | B2 | 12/2003 | Bolze et al. |
| 6,719,049 | B2 | 4/2004 | Sherwood et al. |
| 6,871,713 | B2 | 3/2005 | Meister et al. |
| 7,013,723 | B2 | 3/2006 | Ramakrishnan et al. |
| 7,380,599 | B2 | 6/2008 | Fields et al. |
| 7,805,988 | B2 | 10/2010 | Kasperski et al. |
| 8,324,912 | B2 * | 12/2012 | Waid et al. ............... 324/663 |
| 2002/0139197 | A1 | 10/2002 | Salamitou et al. |
| 2003/0206026 | A1 | 11/2003 | Diakonov et al. |
| 2006/0000603 | A1 | 1/2006 | Zazovsky et al. |
| 2006/0192568 | A1 | 8/2006 | Pasero et al. |
| 2006/0243033 | A1 | 11/2006 | Freemark et al. |
| 2007/0018659 | A1 | 1/2007 | Homan et al. |
| 2007/0133746 | A1 | 6/2007 | Ortiz |

FOREIGN PATENT DOCUMENTS

| | | |
|---|---|---|
| GB | 2453225 A | 1/2009 |
| WO | 03/050529 A1 | 6/2003 |

OTHER PUBLICATIONS

International Search report received in corresponding United Kingdom patent application No. GB0817243.9 dated Jan. 28, 2010.
International Search Report and Written Opinion received in application No. PCT/US07/82221 dated May 5, 2008.
Non-Final Office Action received in U.S. Appl. No. 11/626,461 mail date Jan. 8, 2008.
Final Office Action received in U.S. Appl. No. 11/626,461 mail date Jun. 1, 2009.
Notice of Allowance received in U.S. Appl. No. 11/626,461 mail date Jul. 22, 2010.
Office Action received in U.S. Appl. No. 95/001,756 mail date Nov. 15, 2011.
Action Closing Prosecution (Non Final) received in U.S. Appl. No. 95/001,756 mail date Aug. 8, 2012.

* cited by examiner

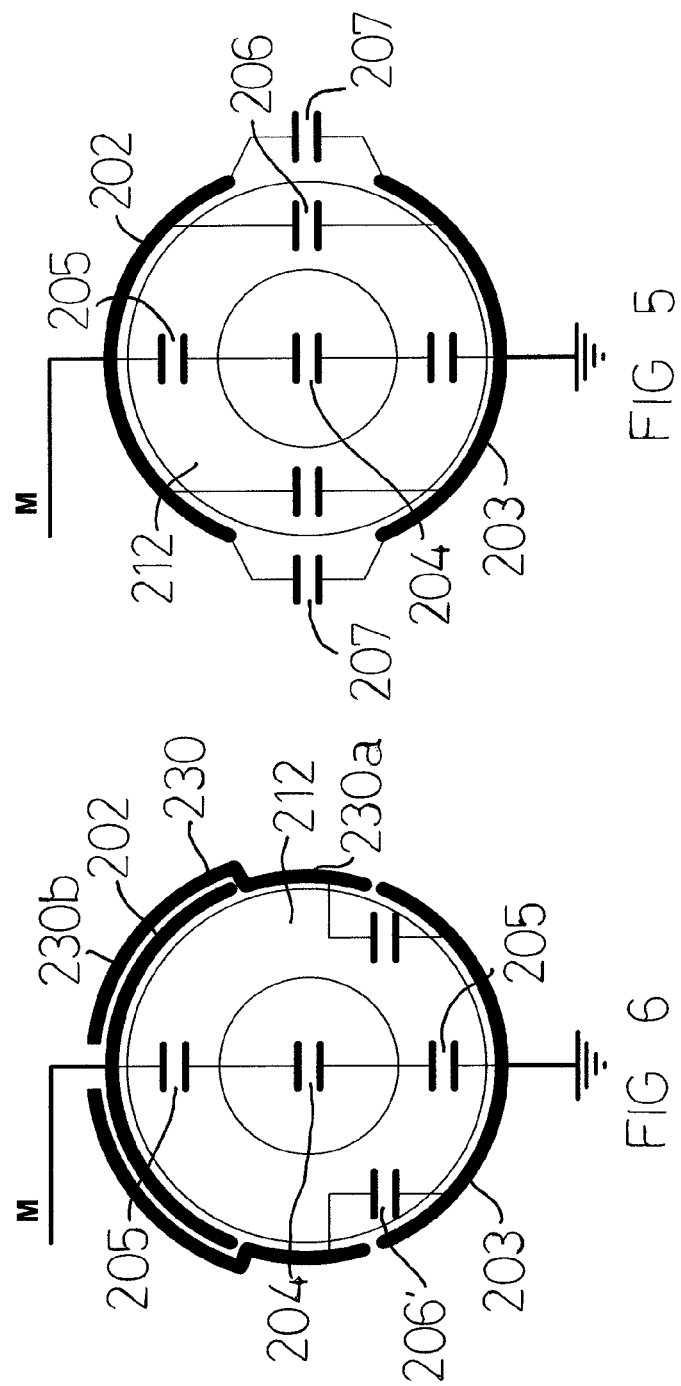

MEASUREMENT TOOL AND METHOD OF USE

CROSS-REFERENCE TO RELATED APPLICATIONS

This application is a continuation of U.S. patent application Ser. No. 12/236,591 filed 24 Sep. 2008, which claims priority to Great Britain Patent Application No. GB0718851.9 filed on 27 Sep. 2007, the contents of each one incorporated herein by reference.

FIELD OF THE INVENTION

This invention relates to a measurement tool and method of use, and in particular to a measurement tool for use in determining a parameter of a stationary or moving fluid. The measurement tool has been designed for use in borehole formation testing and the following description will therefore relate primarily to such applications, but the invention is not thereby limited.

BACKGROUND OF THE INVENTION

Measurement tools are in widespread use in borehole formation testing, for example in boreholes drilled into the earth in order to test for or recover underground reserves of oil and/or gas. Some such tools are carried by the drill string and the measurements are carried out during the borehole drilling operation (so-called "measurement-while-drilling" (MWD) or "logging-while-drilling" (LWD) applications). Other measurement tools are used after the borehole has been drilled, the measurement tools being lowered into the borehole by a cable or wire. In highly deviated wells conveyance may be assisted by semi-rigid tubing or by drill-pipe. Still other measurement tools are deployed downhole for lengthy periods of time with or without a connecting cable and are referred to as permanent or retrievable gauges. These are usually for use in production after the exploration phase is complete.

Tools deployed using cable having one or more electrical conductors are generally referred to as "electric wireline tools". The present invention is most likely to be a part of an electric wireline tool, though its use in MWD/LWD or other downhole applications is not thereby excluded.

One known electric wireline tool is a formation testing tool or "pump-out" tool, which is used to extract a volume of fluid from a formation surrounding a borehole, the fluid being tested in order to evaluate the likely productivity of the oil or gas well.

It is a recognised problem of operating formation testing tools that during the borehole drilling operation the fluid within the formation can be contaminated with drilling fluid (or "mud") filtrate typically comprising liquid and other materials. In order to obtain valuable test results it is of prime importance that the formation fluid used for analysis represents virgin formation fluid with little or no contamination from fluids used in the borehole drilling operation.

Drilling fluid is generally divided into oil base mud (OBM) and water base mud (WBM). The drilling fluid pressure is maintained higher than that of the formation, and as a result the drilling fluid seeps into the formation, the seeping fluid being known as filtrate. Fine particles that cannot penetrate the formation are left behind on the borehole wall and build up to form a filter (or "mud") cake. This is relatively impermeable and forms a skin substantially preventing further ingress of fluid. The filtrate displaces virgin formation fluid from the vicinity of the borehole wall, until a stable 'invaded zone' results. Depending on the virgin fluid, the type of mud and the formation composition and structure, different degrees and depth of invasion occur into the formation.

The formation fluid may naturally contain a large percentage of water, of some salinity. Water base mud is predominantly water but need not have the same salinity. Although perfect oil base mud has very little water, in practice it may contain as much as 40% water. Filtrate may include formation water from other depths in the borehole that has mixed into the mud.

DESCRIPTION OF THE PRIOR ART

Traditionally, operators wishing to extract a volume of fluid from a formation surrounding a borehole in order to evaluate the likely productivity of the well utilised drill stem testing, in which the formation fluid was allowed to flow or was pumped to the surface for testing. This practice has become less desirable primarily because of the harmful environmental impact of needing to flare-off excess gas. Also, there is difficulty in bringing the fluid to the surface from particular wells, especially sub-sea wells. Furthermore, the pressure and temperature of the fluid changes during its movement through the borehole to the surface, and these pressure and temperature changes can cause changes in the consistency of the fluid (i.e. the fluid may separate out into oil, water and gas or otherwise change its material characteristics) which may invalidate the subsequent test.

To overcome the problems associated with flowing the formation fluid directly to the surface, formation testing tools have been developed which can undertake at least some of the tests downhole. One such formation testing tool is described in U.S. Pat. No. 5,602,334, the tool including measurement tools able to measure selected parameters of the formation fluid downhole. This formation testing tool also includes containers which can be filled with formation fluid for transportation to the surface for additional testing if desired.

It is of course necessary that formation testing tools such as that of U.S. Pat. No. 5,602,334 be able to determine whether the fluid being pumped out of the formation is virgin formation fluid, or is contaminated formation fluid, so that the tests are conducted only upon virgin formation fluid, and only virgin formation fluid is collected in the containers. For present purposes "virgin" means having as little contamination as possible, and certainly below some threshold of acceptability.

Many different parameters are desired to be tested downhole, some of which assist in determining whether the fluid is virgin or contaminated, and others which assist the operator in assessing the likely productivity of the formation.

A parameter which can be measured downhole is the electrical resistivity of the fluid. This parameter is often used to determine whether the fluid is virgin or contaminated because the electrical resistivity of oil is significantly different to that of water base muds. US patent application 2007/0018659 discloses a measurement tool for use in a formation testing tool, the tool measuring the resistivity of the formation fluid flowing through it.

In US patent application 2007/0018659 the resistivity of the formation fluid is tested as the fluid is flowing through a pipe, and this is a particularly desirable feature of measurement tools used in formation testing tools where the pipe can lie within the formation testing tool. The pipe should preferably be substantially linear and free from constrictions, bends or voids which would induce pressure changes into the fluid, which pressure changes may affect the consistency of the fluid and thereby lead to a different test result than would be obtained upon fluid within the formation.

Another parameter which can be measured downhole is pressure, typically as part of a draw-down and build-up pressure test which can be used to determine the mobility (permeability divided by viscosity) of a formation and therefore help to assess the likely productivity of the formation.

Yet another parameter is the chemical constituents of the fluid, which can be used to determine whether the formation fluid at one depth of the borehole is the same as that at another depth, any chemical dissimilarity between the formation fluids at different depths indicating that the formation is not contiguous and is instead made up of discrete reservoirs which will make the oil and/or gas more difficult and expensive to recover. Chemical dissimilarity can also be used to differentiate virgin fluid and filtrate.

The likely productivity of an oil and/or gas reservoir is a very valuable assessment for operators to make as this determines the likely value of the reservoir to the operator. It is an object of this invention to provide a measurement tool which can be used in a formation testing tool and which is able to test more relevant parameters of the formation fluid and/or which is able to test the relevant parameters more accurately and reliably, so that the operator can make a more accurate assessment of the productivity of a particular reservoir.

It is another object of the present invention to assist in distinguishing virgin formation fluid from invasion filtrate ("contamination"), recognising that both the water and oil components in the invaded zone are often a mixture of residual virgin fluid and filtrate, and that virgin fluid beyond the invaded zone may have water or oil similar to that of the mud filtrate.

SUMMARY OF THE INVENTION

According to the first aspect of the invention, there is provided a measurement tool for measuring the dielectric constant of a fluid within a pipe, the pipe being electrically insulating, the tool having:
a pair of capacitor plates mounted adjacent to the pipe,
a signal generator which can deliver an alternating electrical signal to at least one of the capacitor plates, and
a detector for measuring a signal dependent upon the electrical capacitance between the capacitor plates.

By suitable arrangement of the capacitor plates, the measured signal will depend upon the capacitance of the fluid within the pipe, and the capacitance of the fluid can be used to determine the dielectric constant of the fluid.

Preferably, the pair of capacitor plates are mounted outside of the pipe, so that there is no direct contact between the plates and the fluid. The capacitance measured will therefore depend upon the capacitance of the fluid and the capacitance of the pipe. Using an insulating pipe with a high dielectric constant in an appropriate arrangement with the capacitor plates will result in the measured signal being dependent primarily upon the capacitance of the fluid.

It has been recognised that the dielectric constant of predominantly oil or gas virgin formation fluid is significantly different to the dielectric constant of water base muds. The dielectric constant of virgin formation fluid is also often measurably different to the dielectric constant of oil base muds because of their differing water contents, so that the present measurement tool can be used to assist determination of whether the fluid within the pipe is contaminated or is virgin formation fluid suitable for further testing. Also, the dielectric constant of virgin formation fluid can provide valuable information to the operator.

The capacitor plates may surround respective parts of the pipe so that the capacitance is measured "along" the pipe. Alternatively, the capacitor plates may be mounted to opposed sides of the pipe, so that the capacitance is measured "across" the pipe. In embodiments in which the pipe is of circular cross-section the capacitor plates can be annular or part-annular.

Desirably, the dielectric constant of the pipe is at least eight. The pipe therefore has a much higher dielectric constant than oil (which typically has a dielectric constant of around two) and is acceptable in relation to water (which has a dielectric constant ranging from around twenty to around eighty one according to factors like temperature and contamination.

There can be three capacitor plates. The use of three capacitor plates can enhance the signal strength of the apparatus and increase the volume of measured fluid.

The three capacitor plates can be arranged along the length of the pipe, with the signal generator connected to the central, driven, capacitor plate, and with the other two capacitor plates connected to ground.

Preferably, the signal generator is connected to its capacitor plate by a screened signal wire and the signal generator is connected to a metallic screen by a screening connector, the screening connector being connected to an operational amplifier configured as a "voltage follower", so that the voltage upon the screening connector is matched to that of the signal wire. Ideally, the screening connector also surrounds the signal wire for at least part of its length, in the form of a coaxial or screened cable or the like. Because the voltages of the signal wire and the screening connector are matched, the capacitance of the coaxial or screened cable can be ignored, and yet the screening connector protects the signal wire from extraneous electrical signals.

Preferably, at least the driven capacitor plate and pipe are surrounded by one or more metallic plate(s) acting as a focussing plate, connected by way of a voltage follower to the same potential as the driven capacitor plate. The focussing plate(s) acts to reduce the desensitising effects of portions of the pipe dielectric material exposed between the capacitor plates. The focussing plate(s) also shields the capacitor plate(s) from extraneous electrical signals.

Desirably, the focussing plate(s) is connected to the metallic screen so that they may share the same voltage follower. Desirably the signal generator and voltage follower circuits are at one end of the screened wire and the capacitor plates and focussing plate(s) at the other end.

The signal which is measured can be the electrical voltage upon, and the electrical current flowing through, the signal wire, which together can be used to determine the capacitance in known fashion.

The frequency of the alternating signal is chosen to suit the application, it being understood that particular frequency ranges will be better suited to determining changes in the capacitance of particular fluids at particular temperatures. For a measurement tool for use in a formation testing tool the presently preferred frequency is 16 kHz, though other frequencies are expected to be suitable for particular configurations and apparatus.

According to a second aspect of the invention there is provided a measurement tool for measuring the dielectric constant of a fluid, the measurement tool having a wall, the wall of the measurement tool being electrically insulating, the tool having:

a pair of capacitor plates mounted adjacent to the wall,
a signal generator which can deliver an alternating electrical signal to at least one of the capacitor plates, and
a detector for measuring a signal dependent upon the electrical capacitance between the capacitor plates.

The arrangement according to the first aspect of the invention, with the measurement tool located around a pipe within which the fluid is located, is reversed in the second aspect, so that the measurement tool is located inside a sensing element which is immersed in the fluid.

Thus, the inventors have realised that the invented tool can also be used in applications such as production logging, i.e. the determination of the fluid characteristics of the oil and gas being produced by a well, perhaps during the lifetime of the well, or at least for an extended period of time. Such ongoing testing of a production well is used in "intelligent wells", in which data concerning the production fluid is continuously or regularly assessed.

In such applications, it may be preferable to utilise the invention according to its second aspect, i.e. it may be more practical to immerse the measurement tool within the fluid in the well, rather than seek to pass some or all of the fluid along the pipe of a measurement tool, which may unnecessarily restrict the flow of fluid.

Alternative, preferable and desirable features of the invention in its second aspect correspond to the alternative, preferable and desirable features of the invention in its first aspect.

According to the first aspect of the invention there is also provided a method of measuring the dielectric constant of a fluid within a pipe, the method comprising the steps of:
{i} providing an electrically insulating pipe and introducing the fluid into the pipe;
{ii} mounting a pair of capacitor plates adjacent to the pipe,
{iii} connecting a signal generator to at least one of the capacitor plates and delivering an alternating electrical signal to said at least one of the capacitor plates,
{iv} providing a detector to measure a signal dependent upon the electrical capacitance between the capacitor plates, and
{v} using the signal measured by the detector to determine the dielectric constant of the fluid. According to the second aspect of the invention there is provided a method of measuring the dielectric constant of a fluid, the method comprising the steps of:
{i} providing a measurement tool having an electrically insulating wall and a pair of capacitor plates mounted adjacent to the wall,
{ii} connecting a signal generator to at least one of the capacitor plates and delivering an alternating electrical signal to said at least one of the capacitor plates,
{iii} providing a detector to measure a signal dependent upon the electrical capacitance between the capacitor plates,
{iv} introducing the measurement tool to the fluid, and
{v} using the signal measured by the detector to determine the dielectric constant of the fluid.

The method steps need not be sequential and their order can be amended if required, and/or some of the steps can be concurrent.

The measurement tool can also include an apparatus for determining a signal indicative of the electrical resistivity of the fluid. Electrical resistivity can be used to distinguish between filtrate and virgin formation fluid due to their different salinities and hydrocarbon-water ratios, and can be used to obtain valuable information in its own right. For example, if the virgin fluid is found to be water and not oil or gas, the operator can avoid subsequently producing it. Generally speaking, when water is the continuous phase a resistivity reading can be obtained. When oil or gas is the continuous phase a dielectric reading can be obtained. The measurements of dielectric constant and resistivity are thus complementary. Moreover, as fluid flows from the formation its composition may exhibit short term fluctuations and these may be used as a further differentiator and indicator of transition from filtrate to virgin fluid.

Desirably, the measurement tool further includes:
a first toroid surrounding a part of the pipe,
a second toroid surrounding a part of the pipe, separate from the first toroid,
a second signal generator connected to the first toroid for delivering an alternating electrical current to the coil of the first toroid,
a second detector connected to the second toroid for determining the current flowing through the coil of the second toroid, and
a return path conductor connected to the fluid in the pipe either side of the two toroids.

Conducting fluid in the pipe and the return path conductor together form a closed conducting loop threaded through the two toroids, thereby creating a coupled pair of transformers by acting as a resistive secondary turn to the first toroid and a primary turn to the second toroid. The resistance is principally due to the fluid as it can be arranged for the return conductor to be of relatively low resistance, such as by making it of metal. For convenience, the metalwork of the tool which necessarily surrounds the toroids can be used as the return path conductor, although a direct wired connection (perhaps in addition to the metalwork of the tool) may be preferred in some applications.

The current flowing through the first toroid induces an electrical current to flow within the pipe and within the fluid inside the pipe. Because the pipe is an electrical insulator the current induced in the pipe is very small or effectively zero. The current flowing in the fluid is directly dependent upon the driving current and the resistivity of the fluid in the pipe. Any current flowing within the fluid induces a current to flow within the coil of the second toroid, the induced current being directly dependent upon the current flowing within the fluid. A comparison of the current flows through the first toroid and the second toroid will therefore provide a direct measure of the resistivity of the fluid within the pipe.

Reference is made above to a second signal generator to distinguish this from the first signal generator used in the dielectric constant measurement. Thus, it is recognised that the optimum frequency range of the alternating signal for the dielectric constant measurement will not necessarily be the same as the optimum frequency range for the resistivity measurement. In certain applications, however, these ranges may overlap in which case the first signal generator and the second signal generator can be the same component. Similarly, the term "second detector" is used to distinguish from the first detector used in the dielectric constant measurement, since these detectors will in most applications be different components.

It will be noted that it is desirable that the pipe containing the fluid (according to the first aspect of the invention) for both of the dielectric constant measurement and the resistivity measurement is the same pipe, and it is a benefit of the present invention that both of these measurements can be performed (perhaps continuously) on substantially the same volume of fluid, if desired. Thus, changes in the material consistency or constituents of the fluid which affect both its dielectric constant and its electrical resistivity can be determined by measurement of both of these parameters at substantially the same time, whereas changes in consistency and/or constituents which affect only one of these parameters will be determined only by measurement of that particular parameter. This will provide valuable additional information to operators over two unrelated measurement tools.

Accordingly, in its first aspect the invention can provide a method of measuring the dielectric constant and the electrical resistivity of a fluid within a pipe, the method comprising the steps of:
{i} providing an electrically insulating pipe and introducing the fluid into the pipe;
{ii} mounting a pair of capacitor plates adjacent to the pipe,
{iii} connecting a first signal generator to at least one of the capacitor plates and delivering an alternating electrical signal to said at least one of the capacitor plates,
{iv} providing a first detector to measure a signal dependent upon the electrical capacitance between the capacitor plates,
{v} using the signal measured by the first detector to determine the dielectric constant of the fluid,
{vi} locating a first toroid adjacent to a part of the pipe,
{vii} locating a second toroid adjacent to another part of the pipe,
{viii} connecting a second signal generator to a coil of the first toroid and delivering an alternating electrical current to the coil of the first toroid,
{ix} connecting a second detector to a coil of the second toroid for measuring the current flowing through the coil of the second toroid,
{x} providing a return path conductor connected to the fluid in the pipe to either side of the two toroids,
{xi} using the current measured by the second detector to determine the electrical resistivity of the fluid.

In its second aspect the invention can provide a method of measuring the dielectric constant and the electrical resistivity of a fluid, the method comprising the steps of:
{i} providing a measurement tool having an electrically insulating wall and a pair of capacitor plates mounted adjacent to the wall,
{ii} connecting a signal generator to at least one of the capacitor plates and delivering an alternating electrical signal to said at least one of the capacitor plates,
{iii} providing a detector to measure a signal dependent upon the electrical capacitance between the capacitor plates,
{iv} locating a first toroid adjacent to a part of the wall,
{v} locating a second toroid adjacent to another part of the wall,
{vi} connecting a second signal generator to a coil of the first toroid and delivering an alternating electrical current to the coil of the first toroid,
{vii} connecting a second detector to a coil of the second toroid for measuring the current flowing through the coil of the second toroid,
{viii} providing a return path conductor to either side of the two toroids,
{ix} introducing the measurement tool to the fluid,
{x} using the signal measured by the detector to determine the dielectric constant of the fluid,
{xi} using the current measured by the second detector to determine the electrical resistivity of the fluid.

The method steps need not be sequential and their order can be amended if required, and/or some of the steps can be concurrent.

In preferred methods the pair of capacitor plates are located between the two toroids and the dielectric constant and the electrical resistivity are measured simultaneously or substantially simultaneously. This enables the two parameters to be measured on the same or substantially the same body of fluid, even if the fluid is flowing.

The alternating electrical signal and the alternating electrical current could be of sinusoidal or square waveform but this is not necessary for the performance of the invention, and any suitable alternating waveform can be used.

In the embodiments according to the first aspect in which the same pipe is used for the measurement of both parameters, it must satisfy the separate requirements for each parameter, as above indicated. A ceramic pipe made from silicon nitride ($Si_3N_4$) has been found to have a dielectric constant and a resistivity which matches the requirements of the measurement tool, and a suitable material is obtainable from Ceradyne Inc., of 3169 Red Hill Avenue, Costa Mesa, Calif. 92626, USA, and sold under the trade name CERALLOY 147-31N. In addition, a pipe of this material having an internal cross-sectional diameter of around 6.4 mm (¼ inch) and a wall thickness of 3.2 mm (⅛ inch) can withstand internal pressures of more than $1.7 \times 10^8$ Pa (25,000 p.s.i.). Since these are the pressures typically encountered at borehole depths of around 10 km it is possible to surround the pipe by air rather than requiring some incompressible material which might adversely affect the measurement of dielectric constant or resistivity, or render construction more difficult and less reliable.

The measurement tool has additional benefits in multi-flow formation testing tools such as that described in U.S. Pat. No. 7,805,988. In this formation testing tool two (or more) fluid flows from the formation are kept separate and are tested separately, and a measurement tool of the present invention could be arranged in each flow line and direct comparisons between the two fluids could be made as desired. In particular a first fluid flow can be the primary flow for measurement and sampling purposes and a second fluid flow can be arranged to come from a different (but ideally adjacent) part of the formation to that of the first flow. For different fluid flows which leave the formation at the same time it is usually desirable to minimise any difference in the time at which the testing is undertaken, and ideally the different fluid flows should be tested at exactly the same time so that measured differences over time in the first and second fluid flows can be used as an indicator of the first fluid changing to virgin fluid (for example). It is possible to minimise (or eliminate) any differences in the time of testing using a multi-flow testing tool such as that of U.S. Pat. No. 7,805,988 by arranging the pipes for the different fluid flows to lie alongside one another, and to be of substantially identical lengths.

DESCRIPTION OF PREFERRED EMBODIMENTS

Figure 2:
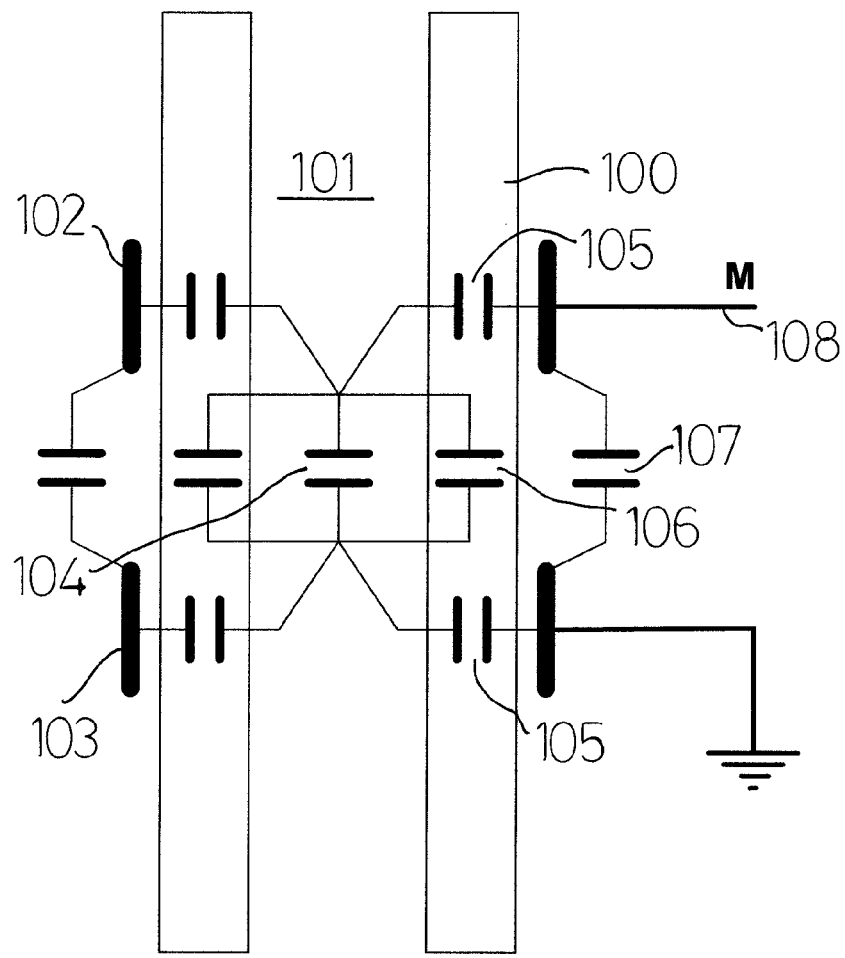
Figure 3:
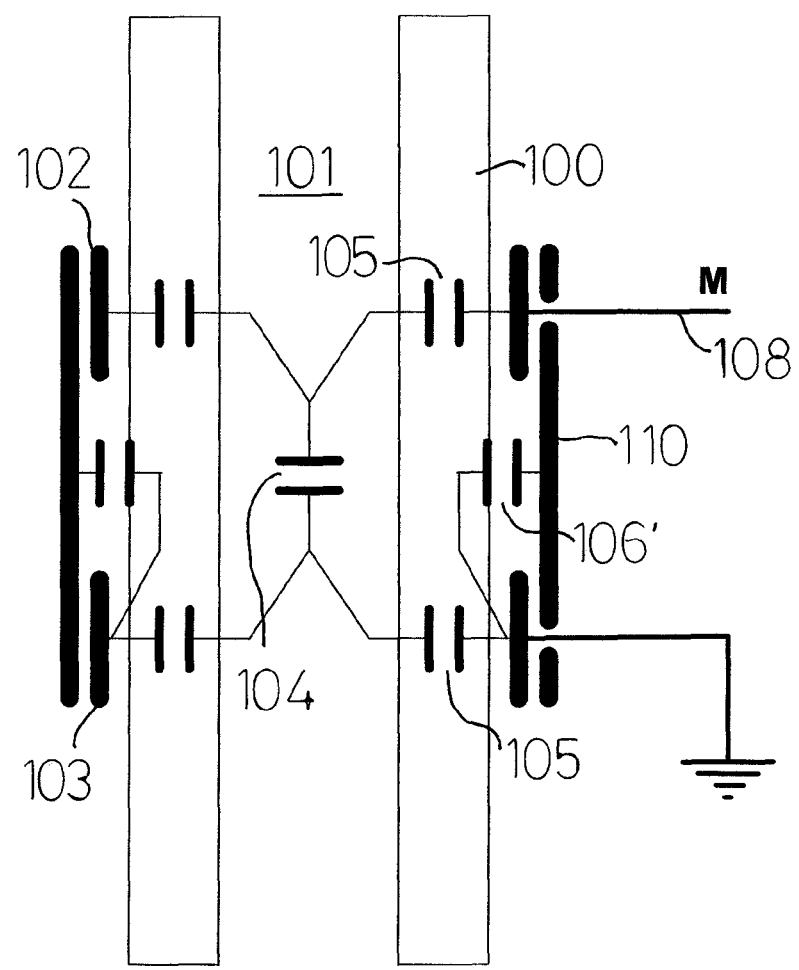
Figure 4:
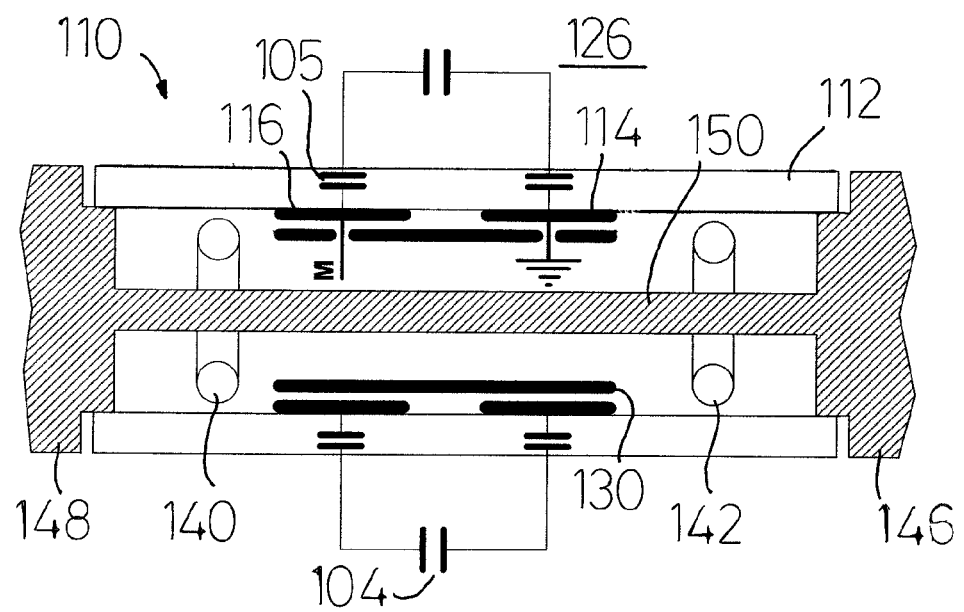

The invention will now be described in more detail, by way of examples, with reference to the accompanying drawings, which show:

FIG. 1 a longitudinal cross-section through the pipe of a measurement tool according to an embodiment of the first aspect of the invention;

FIG. 2 a schematic representation in transverse cross-section of the capacitance of the fluid and pipe as measured by the tool of FIG. 1;

FIG. 3 a representation as FIG. 2 showing the effect of a metallic focussing plate;

FIG. 4 a transverse cross-section through a measurement tool according to the second aspect of the invention;

FIG. 5 a schematic representation in transverse cross-section of the capacitance of the fluid and pipe as measured in an alternative embodiment of the first aspect of the invention; and FIG. 6 a schematic representation as FIG. 5 showing the effect of a focussing plate.

DETAILED DESCRIPTION

According to the first aspect of the invention, the measurement tool 10 has a pipe 12. The pipe 12 is made of an electrically insulating material. The pipe 12 is also substantially linear and has a substantially uniform cross-section along its length, so that the pipe does not induce unwanted pressure changes into a fluid flowing therealong. The ends of the pipe are not shown, but in known fashion the ends are fitted with connectors by which the pipe may be sealingly connected to adjacent pipes or couplings. When used in a formation testing tool for example the pipe 12 may be connected to adjacent pipes within the body of the formation testing tool, the adjacent pipes perhaps being parts of other measurement tools for measuring other parameters of the fluid.

In this embodiment the pipe is of circular cross-section, with an outer diameter of approx. 12.7 mm (approx. ½ inch), and an inner diameter of approx. 6.4 mm (approx ¼ inch).

The tool 10 also has three capacitor plates 14, 16, 18, the capacitor plates in this embodiment comprising conductive sleeves surrounding respective parts of the pipe 12. In this embodiment the capacitor plates 14, 16 and 18 are of identical dimensions, but this is not necessarily so.

A signal generator 20 is connected to the central capacitor plate 16 by a signal wire 22, whereby the signal generator 20 delivers an alternating electrical signal to the capacitor plate 16. The capacitor plates 14 and 18 are connected to ground, and the voltage which builds up on the capacitor plate 16, and the current which flows onto and off from the capacitor plate 16 during each cycle, is directly dependent upon the capacitance of the system.

A detector 24 is able to measure the voltage upon the signal wire 22 (relative to ground), and also the current flowing along the signal wire 22, and can use these signals to determine the electrical capacitance of the system. The detector can incorporate a phase-sensitive detector to enhance signal to noise ratio.

The capacitance of the system, namely the capacitance between the capacitor plate 16 and the capacitor plates 14 and 18, is dependent upon the dielectric constant of the material therebetween. In an arrangement such as that shown in FIG. 1, with the capacitor plates arranged along the pipe, the electric field is generated between the facing ends of the capacitor plates 16 and 14, and also between the facing ends of the capacitor plates 16 and 18. Part of the electric field lies within the wall of the pipe 12, part within the fluid 26 inside the pipe 12, and part within the material surrounding the pipe, and so the capacitance of the system depends upon the dielectric constant of the pipe, the fluid, and the material surrounding the pipe.

In this embodiment the pipe 12 is made from silicon nitride which has a dielectric constant of approximately eight. Also, the pipe 12 is surrounded by air which has a dielectric constant of one. Accordingly, the capacitance of the system is highly dependent upon the dielectric constant of the fluid 26, and changes in the dielectric constant of the fluid 26 caused by changes in the consistency or constituents of the fluid 26 will cause a change in the capacitance of the system.

The tool 10 can be calibrated (either by calculation or more typically with known fluids 26 at known temperatures), so that the measurement tool 10 can determine the actual dielectric constant of the fluid 26. This will allow the measurement tool 26 to be used quantitatively which will allow the operator to make detailed assessments of the fluid, including for example its chemical constituents. Alternatively, the tool can be used qualitatively to determine changes in the material characteristics (for example identifying the change from contaminated formation fluid to virgin formation fluid) which determinations can be utilised by other measurement tools.

The capacitor plates 14, 16 and 18 are all surrounded by an electrically conductive sleeve 30, usefully of metal. The sleeve 30 is arranged close to the capacitor plates 14, 16, 18 and is here referred to as a focussing plate since its action is to focus or concentrate the electric field within the fluid 26 (see the detailed description below of FIGS. 2 and 3). The focussing plate 30 also provides a screening function by preventing extraneous electrical signals and the dielectric constant of material outside the plate from affecting the charge upon the capacitor plates 14, 16, 18.

In order to enable the capacitance between the focussing plate 30 and the capacitor plate 16 to be ignored, the voltage of the focussing plate 30 is matched to that of the capacitor plate 16. This is achieved by connecting the focussing plate 30 to the signal generator 20 by way of a screening connector 32 and an operational amplifier 34 configured as a voltage follower.

It will be understood that an operational amplifier 34 in voltage follower mode provides the same voltage at its output as that at its input and since in this embodiment its input is connected to the signal generator 20 the voltage at the output, and therefore the voltage upon the screening connector 32 and focussing plate 30, matches that of the signal generator 20. At all times therefore the voltage upon the focussing plate 30 matches that of the capacitor plate 16.

Also, at all times the voltage of the screening connector 32 matches that of the signal wire 22, enabling the signal wire 22 and screening connector 32 to be respective parts of a coaxial or screened cable 36 for at least part of their length, with the screening connector 32 forming the shield surrounding the signal wire of the coaxial cable 36 in known fashion. Once again, because of their matched voltages, the capacitance between the signal wire 22 and the screening connector 32 can be ignored.

The frequency applied by the signal generator 20 can be set as required, and can be varied during use of the measurement tool 10 if desired. The optimum frequency will depend upon the application, and may depend for example upon the range of dielectric constants expected for the fluid 26, and the other variable parameters such as temperature of the fluid 26. A suitable frequency for use in one practical formation testing tool has been found to be 16 kHz.

This measurement tool 10 is not only able to measure dielectric constant, but also resistivity. Importantly, the measurement tool 10 uses only one pipe 12 for the two measurements, so that the measurements can be carried out substantially simultaneously on the same volume of fluid 26.

To carry out a resistivity measurement upon the fluid, the measurement tool 10 has a first toroid 40 surrounding a part of the pipe 12 and a second toroid 42 surrounding another part of the pipe 12, the toroids 40,42 being separated along the length of the pipe. The toroids are of conventional form, comprising a loop of iron (or other ferromagnetic material) surrounded by an electrical coil.

A second signal generator 44 is connected to the electrical coil 38 of the first toroid 40 and delivers an alternating electric current to the electrical coil 38 (only a part of the coil 38 is shown in FIG. 1). Passing an electric current through the coil induces a magnetic field in the first toroid which in turn induces an electric current to flow in any conductor located within the first toroid. The pipe 12 is located within the first toroid 40 and since the pipe 12 is an insulator a current will be induced to flow within the fluid 26. The tool 10 includes a conductive return path comprising a pair of electrodes 46 and 48 connected by a wire 50. The electrodes 46 and 48 are located within the pipe 12 so that they directly contact the fluid 26. Preferably, the electrodes 46, 48 are embedded into the wall of the pipe 12 so that they do not induce turbulence or any pressure changes in the fluid 26 as it flows therepast.

It will be understood that the toroids can be placed to either side of the focussing plate 30. The metal housing of the cell or tool can in some embodiments provide part or all of the return path and this would avoid the requirement for a separate wire 50 and reduce the complexity of the tool.

Desirably the capacitor plates 14,16,18 and focussing plate 30 are made from non-strongly magnetic materials so as not to increase the toroids' leakage flux.

Any current flowing through the fluid 26 between the electrodes 48 and 46 will induce a current to flow around the coil 54 of the second toroid 42 (only a part the coil 54 is shown in FIG. 1). That current is detected by a second detector 52, the current flowing through the coil around the second toroid being directly related to the current flowing within the fluid, and therefore directly related to the resistivity of the fluid 26. The detector may incorporate a phase sensitive detector to enhance signal to noise ratio.

The measurement tool 10 can be calibrated (again by calculation or by experimentation with fluids of known resistivities) so that it can be used quantitatively, or it may be used qualitatively to determine changes in the resistivity of the fluid 26.

FIGS. 2 and 3 show representations of the tool to demonstrate the advantage of a metallic focussing plate such as 30. Specifically, the action of the focussing plate and the role of the pipe dielectric constant may be understood by reference to the simplified model of the capacitance distribution in the cell as shown in FIG. 2. It will be understood that these capacitances in reality represent the distribution of electric potential within the cell as may be calculated from electromagnetic theory by one practised in the art. It will also be understood that the present invention is not dependent upon the capacitance model.

A pipe 100 surrounds fluid 101. Annular capacitance plate 102 is connected to the signal generator M at 108 and annular capacitance plate 103 is connected to ground (the capacitance plates 102, 103 therefore replicating the capacitance plates 16, 14, or 16, 18, of FIG. 1). The fluid capacitance to be measured is that represented by the notional capacitor 104. This fluid capacitance is in parallel with the axial capacitance 106 of the pipe wall. There is also radial series capacitance 105 due to the pipe wall, and stray capacitance 107 exterior to the pipe between the electrodes. All capacitances other than 104 will affect the sensitivity and interpretation of the measurement.

In order to maximise the sensitivity to the capacitance 104, it is desirable to maximise series capacitance 105, which can be achieved by maximising the pipe material's dielectric constant. On the other hand this will increase parallel capacitance 106 which is undesirable.

FIG. 3 demonstrates the effect of adding an annular focussing plate 110, the focussing plate 110 being held at the same potential as capacitor plate 102, preferably by a voltage follower as described in relation to the focussing plate 30 of FIG. 1. With the focusing plate 110 present, the axial capacitance 106 is replaced by a radial capacitance 106' and the stray capacitance 107 is eliminated. The measurement is now just of the desired capacitance 104 in series with the radial capacitance 105. With a high dielectric constant pipe material, the measurement will be very sensitive to changes in fluid dielectric constant.

It will furthermore be understood that the focussing action described requires only that the focussing plate 110 cover the dielectric material in the axial space between the capacitor plates 102 and 103. Similarly for the arrangement of FIG. 1, so that if the screening function of the plate 30 is not required the focussing plate could by shortened to fill the axial space between plates 14 and 16 and the axial space between plates 16 and 18, which would maximise the sensitivity to the fluid capacitance as desired.

FIG. 4 demonstrates the invention according to its second aspect, it being appreciated that the dielectric (and resistivity) measurement can be made exterior to the wall 112 of the measurement tool 110 when the capacitor plates (and preferably also focussing plate(s)) are within the wall 112 and the fluid 126 to be tested is outside the wall. Such a configuration has wide applicability to measurement of fluid properties in boreholes such as during production in production logging tools and in permanent deployment as in an intelligent well.

Capacitor plate 116 of the embodiment of FIG. 4 performs the same function as capacitor plate 16 in the embodiment of FIG. 1, and similarly for the capacitor plates 114 and 14, and also for the other components 130, 140, 142, 146 and 148 which perform the same functions as the components 30, 40, 42, 46 and 48 respectively. Because of the similarity of many of the components of the embodiment of FIG. 4 to the components of the embodiment of FIG. 1, it is believed that a skilled person does not require a detailed description of FIG. 4.

Whilst FIG. 4 shows only two capacitor plates 114 and 116, it will be understood that another embodiment could utilise three capacitors along the sensing element in a similar arrangement to that of FIG. 1, with the signal generator (M in FIG. 4) being connected to the central capacitor and the other two capacitors being connected to ground. Whilst FIG. 4 does not show the details of the signal generator M and related componentry, it will be understood that components identical or similar to the signal generator 20, signal wire 22, detector 24, screening connector 32, operational amplifier 34 and perhaps also the coaxial cable 36 of the embodiment of FIG. 1 could be provided within the measurement tool 110.

FIG. 4 also shows the notional capacitance 104 of the fluid 126 which is desired to be measured, and also the notional series capacitance 105, using the same reference numerals as FIGS. 2 and 3.

In the embodiment of FIG. 4 the wall 112 is tubular and the measurement tool 110 can be surrounded by the fluid 126. In alternative embodiments the measurement tool is adapted to lie alongside the body of fluid, for example being mounted into the wall of a conduit for the fluid.

FIGS. 5 and 6 represent a measurement tool in which the capacitance plates 202, 203 are arranged across the pipe 212. FIG. 5 corresponds to FIG. 2 and again is a generalised approximation to the actual distributed field structure in the cell. The capacitance between the capacitor plates 202 and 203 is a series measurement comprising the capacitance through the wall material 205 and the capacitance of the fluid 204. This capacitance is shunted by the capacitance around the wall material 206 and external stray capacitance 207.

FIG. 6 corresponds to FIG. 3, and shows the effect of a focussing plate 230. The focussing plate 230 is driven by the signal generator M to be at the same potential as the capacitor plate 202. This eliminates the effect of external capacitance and by altering the internal field largely reduces the shunt capacitance 206 to a capacitance 206' between the focussing plate 230 and the grounded capacitor plate 203. This results in a measurement closer to the simpler series structure of capacitances 205 and 204.

FIGS. 5 and 6 represent cross-sectional views through the measurement tool. The longitudinal length of the driven capacitor plate 202 (i.e. the length in the direction along the longitudinal axis of the tool) is chosen to suit the application. The longitudinal dimension of the focussing plate 230 is preferably greater than the longitudinal dimension of the driven capacitor plate 202.

FIG. 6 shows a plate 230 which provides both the focussing and screening functions as in the embodiments of FIGS. 1, 3 and 4. The region 230a of the plate 230 which lies between the capacitor plates 202 and 203 provides the focussing action, whilst the region 230b of the plate 230 which overlies the driven capacitor plate 202 provides the screening function. In addition, the plate 230 extends beyond the edges of the driven capacitor plate 202 in the longitudinal direction.

It has been found to be beneficial that the grounded capacitor plate 203 extends longitudinally beyond the focussing plate 230 and the driven capacitor plate 202, and in particular that the grounded capacitor plate 203 completely surrounds the measurement tool beyond the ends of the focussing plate 230. Thus, in the orientation of FIG. 6 the grounded capacitor plate 203 beneficially extends into and out of the paper beyond the driven capacitor plate 202 and the focussing plate 230, and surrounds the pipe 212 both above and below the focussing plate 230.

It will also be noted that the focussing plate 230 is stepped around the driven capacitor plate 202 so that its region 230a lies closer to the pipe 212 between the capacitor plates 202 and 203. This has been found to improve the focussing action.

In a practical embodiment the capacitor plates 202, 203 and the focussing plate 230 are provided by a strip of flexible double-sided printed circuit board material, with the driven capacitor plate 202, the region 230a of the focussing plate 230 and the grounded capacitor plate 203 being formed on one side thereof (with the region 230a of the focussing plate surrounding the driven capacitor plate 202, and the grounded capacitor plate 203 surrounding the region 230a of the focussing plate). The screening region 230b of the focussing plate 230 is formed on the other side of the printed circuit board, and is connected to the region 230a of the focussing plate 230 by vias through the board. The flexible printed circuit board can be wrapped around the measurement tool with the driven capacitor plate 202, the region 230a of the focussing plate 230 and the grounded capacitor plate 203 preferably in contact with the pipe. The region 230b of the focussing plate encloses the driven capacitor plate 202 and is separated from the driven capacitor plate 202 by the substrate material of the printed circuit board.

Extending the grounded capacitor plate 203 beyond the longitudinal ends of the focussing plate 230, and passing the grounded capacitor plate 203 circumferentially around the pipe 212 provides a defined environment for the driven capacitor plate 202, within which the capacitance of the fluid is measured. This also helps to reduce or avoid any field distortion which might occur if the fluid being measured is conductive and is in engagement with electrically conductive parts of the housing of the measurement tool.

It will be understood that the measurement tool represented by FIGS. 5 and 6 uses capacitor plates 202, 203 mounted at radially spaced positions around the pipe 212 into which the fluid is introduced, so that this embodiment is according to the first aspect of the invention. In another embodiment a structure similar to that of FIG. 4 could be provided, but with the capacitor plates mounted across the measurement tool for use in accordance with the second aspect. Measurement tools in which the capacitor plates are mounted across the tool have been found to be more suitable in certain applications since they have a larger response variation to different fluids in the range of interest, i.e. fluids with dielectric constants in the range of around two to around ten which are typical of downhole fluids in oil drilling applications.

Also, whilst FIGS. 5 and 6 do not show the toroids or other components for measuring the electrical resistivity of the fluid, it will be understood that such componentry could be provided. Alternatively considered, the radial arrangement of the two capacitors 202, 203 of FIGS. 5 and 6 could replace the longitudinal arrangement of the three capacitors 14, 16 and 18 of FIG. 1, without altering the componentry of the electrical resistivity measurement. Furthermore, the signal generator 20, detector 24 and related componentry of the embodiment of FIG. 1 could be used with embodiments in which the capacitor plates are arranged across the measurement tool.

It will also be understood that the invention will most often be utilised with fluid flowing along the pipe (or around the tool as applicable), but that the dielectric constant and electrical resistivity measurements could also be taken upon a stationary fluid if desired.

What is claimed is:

1. A measurement tool for measuring the dielectric constant and the electrical resistivity of a fluid, the measurement tool having a wall, the wall of the measurement tool being electrically insulating, the wall having a first side and a second side, the measurement tool being adapted for use with the fluid to the first side of the wall, the measurement tool having:
   a pair of capacitor plates mounted adjacent to the second side of the wall,
   a first signal generator for delivering an alternating electrical signal to at least one of the capacitor plates,
   a first detector for measuring a signal dependent upon the electrical capacitance between the capacitor plates,
   a first toroid mounted adjacent to a part of the second side of the wall,
   a second toroid mounted adjacent to another part of the second side of the wall,
   the pair of capacitor plates being located between the first and second toroids,
   a second signal generator connected to the first toroid for delivering an alternating electrical current to a coil of the first toroid,
   a second detector connected to the second toroid for determining the current flowing through a coil of the second toroid, and
   a return path conductor adapted for connection to the fluid to either side of the two toroids.

2. A measurement tool according to claim 1 in which the wall is a pipe wall, the measurement tool being adapted for measuring the dielectric constant and the electrical resistivity of a fluid within the pipe, the first and second toroids surrounding respective parts of the pipe.

3. A measurement tool according to claim 2 in which the pair of capacitor plates are mounted outside of the pipe.

4. A measurement tool according to claim 2 in which the capacitor plates are mounted to opposed sides of the pipe.

5. A measurement tool according to claim 2 in which the first signal generator is connected to said at least one of the capacitor plates by a screened signal wire and the first signal generator is connected to an electrically conductive screen by a screening connector, the voltage upon the screening connector being matched to that of the signal wire.

6. A measurement tool according to claim 5 in which the voltage upon the screening connector is matched to that of the signal wire by way of an operational amplifier configured as a voltage follower.

7. A measurement tool according to claim 5 in which the screening connector surrounds the signal wire for at least part of the length of the signal wire.

8. A measurement tool according to claim 1 in which the frequency of the alternating electrical signal delivered by the first signal generator is around 16 kHz.

9. A measurement tool according to claim 2 in which the dielectric constant of the pipe is at least eight.

10. A measurement tool according to claim 2 in which the pipe is made from silicon nitride ($Si_3N_4$).

11. A measurement tool according to claim 2 in which the pipe has a substantially circular internal cross-section.

12. A measurement tool according to claim 11 in which the pipe has an internal cross-sectional diameter of approx. 6.4 mm and a wall thickness of approx. 3.2 mm throughout its length.

13. A measurement tool according to claim 1 in which the first signal generator and the second signal generator are different components.

14. A measurement tool for measuring the dielectric constant and the electrical resistivity of a fluid, the measurement tool having a wall, the wall of the measurement tool being electrically insulating, the measurement tool having:
a pair of capacitor plates mounted adjacent to the wall,
a first signal generator for delivering an alternating electrical signal to at least one of the capacitor plates,
a first detector for measuring a signal dependent upon the electrical capacitance between the capacitor plates,
a first toroid mounted adjacent to a part of the wall,
a second toroid mounted adjacent to another part of the wall,
the pair of capacitor plates being located between the first and second toroids,
a second signal generator connected to the first toroid for delivering an alternating electrical current to a coil of the first toroid,
a second detector connected to the second toroid for determining the current flowing through a coil of the second toroid, and
a return path conductor adapted for connection to the fluid to either side of the two toroids,
in which the wall surrounds the capacitor plates and the toroids whereby the measurement tool is adapted for immersion in the fluid.

15. A measurement tool according to claim 14 in which the capacitor plates are mounted to opposed sides of the tool.

16. A measurement tool according to claim 14 in which the first signal generator is connected to said at least one of the capacitor plates by a screened signal wire and the first signal generator is connected to an electrically conductive screen by a screening connector, the voltage upon the screening connector being matched to that of the signal wire.

17. A measurement tool according to claim 16 in which the voltage upon the screening connector is matched to that of the signal wire by way of an operational amplifier configured as a voltage follower.

18. A measurement tool according to claim 16 in which the screening connector surrounds the signal wire for at least part of the length of the signal wire.

19. A measurement tool according to claim 14 in which the dielectric constant of the wall is at least eight.

20. A measurement tool according to claim 14 in which the wall is made from silicon nitride ($Si_3N_4$).

21. A measurement tool according to claim 14 in which the wall is tubular and has a substantially circular external cross-section.

22. A method of measuring the dielectric constant and the electrical resistivity of a fluid, the method comprising the steps of:
{i} providing a measurement tool having an electrically insulating wall and introducing the fluid adjacent to the wall;
{ii} mounting a pair of capacitor plates adjacent to the wall, with the wall separating the capacitor plates from the fluid,
{iii} connecting a first signal generator to at least one of the capacitor plates, the first signal generator delivering an alternating electrical signal to said at least one of the capacitor plates,
{iv} providing a first detector to measure a signal dependent upon the electrical capacitance between the capacitor plates,
{v} using the signal measured by the first detector to determine the dielectric constant of the fluid,
{vi} locating a first toroid adjacent to a part of the wall,
{vii} locating a second toroid adjacent to another part of the wall, with the pair of capacitor plates being located between the first and second toroids, and with the wall separating the first and second toroids from the fluid,
{viii} connecting a second signal generator to a coil of the first toroid and delivering an alternating electrical current to the coil of the first toroid substantially simultaneously with delivering the alternating electrical signal to said at least one of the capacitor plates,
{ix} connecting a second detector to a coil of the second toroid for measuring the current flowing through the coil of the second toroid substantially simultaneously with measuring the signal dependent upon the electrical capacitance between the capacitor plates,
{x} providing a return path conductor connected to the fluid to either side of the two toroids,
{xi} using the current measured by the second detector to determine the electrical resistivity of the fluid.

23. A method of measuring the dielectric constant and the electrical resistivity of a primary fluid, the method comprising the steps of:
{i} providing a measurement tool having a primary electrically insulating wall and introducing the primary fluid adjacent to the primary wall;
{ii} mounting a primary pair of capacitor plates adjacent to the primary wall, with the primary wall separating the primary capacitor plates from the primary fluid, {iii} connecting a first signal generator to at least one of the primary capacitor plates, the first signal generator delivering an alternating electrical signal to said at least one of the primary capacitor plates, {iv} providing a first detector to measure a signal dependent upon the electrical capacitance between the primary capacitor plates, {v} using the signal measured by the first detector to determine the dielectric constant of the primary fluid, {vi} locating a first toroid adjacent to a part of the primary wall, {vii} locating a second toroid adjacent to another part of the primary wall, with the primary pair of capacitor plates being located between the first and second toroids, and with the primary wall separating the first and second toroids from the primary fluid, {viii} connecting a second signal generator to a coil of the first toroid and delivering an alternating electrical current to the coil of the first toroid substantially simultaneously with delivering the alternating electrical signal to said at least one of the primary capacitor plates, {ix} connecting a second detector to a coil of the second toroid for measuring the current flowing through the coil of the second toroid substantially simultaneously with measuring the signal dependent upon the electrical capacitance between the primary capacitor plates, {x} providing a primary return path conductor connected to the primary fluid to either side of the two toroids, {xi} using the current measured by the second detector to determine the electrical resistivity of the primary fluid, {xii} providing a secondary electrically insulating wall and introducing a secondary fluid adjacent to the secondary electrically insulating wall;

{xiii} mounting a secondary pair of capacitor plates adjacent to the secondary electrically insulating wall, with the secondary electrically insulating wall separating the secondary pair of capacitor plates from the secondary fluid, {xiv} connecting a third signal generator to at least one of the secondary capacitor plates, the third signal generator delivering an alternating electrical signal to said at least one of the secondary capacitor plates, {xv} providing a third detector to measure a signal dependent upon the electrical capacitance between the secondary capacitor plates, {xvi} using the signal measured by the third detector to determine the dielectric constant of the secondary fluid, {xvii} locating a third toroid adjacent to a part of the secondary electrically insulating wall, {xviii} locating a fourth toroid adjacent to another part of the secondary electrically insulating wall, with the secondary pair of capacitor plates being located between the third and fourth toroids, and with the secondary electrically insulating wall separating the third and fourth toroids from the secondary fluid, {xix} connecting a fourth signal generator to a coil of the third toroid and delivering an alternating electrical current to the coil of the third toroid, substantially simultaneously with delivering the alternating electrical signal to said at least one of the secondary capacitor plates {xx} connecting a fourth detector to a coil of the fourth toroid for measuring the current flowing through the coil of the fourth toroid substantially simultaneously with measuring the signal dependent upon the electrical capacitance between the secondary capacitor plates, {xxi} providing a secondary return path conductor connected to the secondary fluid to either side of the third and fourth toroids, {xxii} using the current measured by the fourth detector to determine the electrical resistivity of the secondary fluid, {xxiii} comparing the dielectric constant of the primary fluid with the dielectric constant of the secondary fluid, and {xxiv} comparing the electrical resistivity of the primary fluid with the electrical resistivity of the secondary fluid.

* * * * *